US008114453B2

(12) United States Patent
Sen

(10) Patent No.: US 8,114,453 B2
(45) Date of Patent: Feb. 14, 2012

(54) SYNERGISTICALLY HEAT STABLE OIL MEDIA HAVING EICOSA PENTANOIC ACID (EPA) AND DOCOSA HEXAENOIC ACID (DHA)

(75) Inventor: Nirmal Sen, Mumbai (IN)

(73) Assignee: Recon Oil Industries Private Limited, Mumbai (IN)

( * ) Notice: Subject to any disclaimer, the term of this patent is extended or adjusted under 35 U.S.C. 154(b) by 949 days.

(21) Appl. No.: 11/817,973

(22) PCT Filed: Mar. 11, 2005

(86) PCT No.: PCT/IN2005/000079
§ 371 (c)(1),
(2), (4) Date: Sep. 7, 2007

(87) PCT Pub. No.: WO2006/095357
PCT Pub. Date: Sep. 14, 2006

(65) Prior Publication Data
US 2008/0146665 A1   Jun. 19, 2008

(51) Int. Cl.
*A23B 7/16* (2006.01)
*A61K 31/225* (2006.01)
*A61K 31/20* (2006.01)

(52) U.S. Cl. ........ 426/307; 514/547; 514/558; 514/559; 514/560

(58) Field of Classification Search .................. 426/307; 514/547, 558, 559, 560
See application file for complete search history.

(56) References Cited

FOREIGN PATENT DOCUMENTS

| CN | 1397174 A | * | 2/2003 |
| CS | 253339 B1 | * | 11/1987 |

OTHER PUBLICATIONS

Enclosed abstract of CN 1397174 A, hereby known as Ma (2003).*
CS 253339 B1, Skorepa et al., English-translated abstract.*

* cited by examiner

*Primary Examiner* — Kevin E Weddington
(74) *Attorney, Agent, or Firm* — Neifeld IP Law, PC

(57) ABSTRACT

A synergistically heat stable therapeutically active triglyceride and cholesterol controlling oil composition including the usually highly unsaturated Eicosa Pentaenoic Acid (EPA) and Docosa Hexaenoic Acid (DHA). The invention avoids limitations of presently available impure sources of EPA/DHA such as fish oil, algae and the like and provides for a synergistically stable edible oil formulation involving the Eicosa Pentaenoic Acid and Docosa Hexaenoic acid of at least 50% to less than 100% purity in a free of any encapsulated/protected form in combination with synergistically stability contributing oil constituents/ingredients. The invention also provides for benefit applications/uses of the surprising and unexpected heat stability of the beneficial actives EPA and DHA. The invention is therefore directed to serve in possible provision of variety of alternative media including heat stable media for regular consumption of EPA/DHA and provide for maintenance of safe and healthy lifestyle.

6 Claims, No Drawings

SYNERGISTICALLY HEAT STABLE OIL MEDIA HAVING EICOSA PENTANOIC ACID (EPA) AND DOCOSA HEXAENOIC ACID (DHA)

CROSS REFERENCE TO RELATED APPLICATIONS

This application is a U.S. national stage entry of international application PCT/IN2005/000079, filed Mar. 11, 2005.

FIELD OF THE INVENTION

The present invention relates to therapeutically active and health benefiting selective oil formulation and, in particular, to a health benefiting dietary edible oil formulation providing for selective and surprising efficacious and stable retention of highly unsaturated and highly unstable benefit actives Eicosa Pentaenoic acid (EPA) and Docosa Hexaenoic Acid (DHA) even at normal cooking temperature for safe and healthy regular administration/consumption by humans. The dietary edible oil of the invention on one hand avoids the limitations of the use of EPA/DHA in edible oils due to problems of impurity in the sources for such health benefiting actives EPA/DHA presently available and on the other hand takes care of providing the much desired alternative media for regular administration/consumption by humans including such beneficial actives and health preventing cardio-vascular ailments especially those related to high triglyceride and cholesterol in humans including reducing stickiness in blood vessels/walls. The invention is also directed to the finding that EPA/DHA can be heat stable and hence can be advantageous and incorporated in desired amounts in dietary edible oils for cooking purposes and thereby provide for a cooking media good for the health and wellbeing of individuals. The invention is further directed to the method of treating humans for maintaining good health by way of regular consumption/administration into humans of the health benefiting dietary edible oil incorporating such actives EPA/DHA.

BACKGROUND ART

It is well known that accumulation of excess cholesterol and triglycerides are two known predictors for coronary risk and a study conducted by WHO put more emphasis on excess triglyceride which appears to be a stronger predictor for coronary mortality.

It is known that low density lipo-protein (LDL) is a derivative of ingested oil which carry cholesterol to the cells (normal body function) irrespective of body requirements. On the other hand high density Lipo-protein (HDL) another derivative of ingested oil transports back excess cholesterol to liver for disposal.

Therefore in order to maintain cholesterol levels within the normal range and also reduce triglyceride levels in cerum lipid, it is desirable to have reduced level of LDL and increased level of HDL. The ratio that is total cholesterol divided by HDL, is therefore an important criteria, and lower the ratio better it is.

It is anticipated that because of life style changes, a very large section of the population is likely to have cardiovascular problems, and dietary edible oils and their quality and characteristics play an important role in maintaining the health and fitness of humans especially those used to regular consumption of food cooked with such presently available dietary edible oils.

Clinical trials conducted by national institute of nutrition, Hyderabad, India have further proved beyond doubt that conventional ingredients of dietary oils such as Mono saturated fatty acids (MUFA) oleic (n-9), Poly unsaturated fatty acid (PUFA)-linoleic (n-6) and Alpha linolenic acid (ALNA) (n-3) i.e. normal oils and fats used for cooking including safflower oil, soybean oil, groundnut oil, canola oil, etc. cannot reduce triglyceride levels in cerum lipid.

Therefore it has been the requirement in the art to provide dietary cooking oils having beneficial effects namely reduction of LDL and/or increase in HDL or the ratio of cholesterol and direct HDL reduction of triglyceride level and reduction of tendency of platelets to clump and adhere to the blood vessel walls due to lower cholesterol levels and related contraction of the blood vessel themselves would go a long way for overall health care as oils are used daily and by all members of the family.

It is known that Eicosa Pentaenoic Acid (EPA) and Docosa Hexaenoic Acid (DHA) have therapeutic values as actives capable of reducing the cholesterol level in the body and favour maintaining good health conditions especially by safeguarding against coronary risks associated with high triglyceride/cholesterol levels in the body.

However, inspite of the above known therapeutic values of EPA/DHA so far their use has been mostly restricted to its use in encapsulated/protected form as capsules because of possible instability in contact with air/moisture due to its highly unsaturated constitution/characteristic. It is known that heat is extremely damaging to any polyunsaturated oil. It serves to break their precious double bonds changing the oil from a healthy and safe known constitution into an unhealthy unknown constitution. These effects magnify as cooking temperature increases.

The poly unsaturated fatty acids DHA/EPA therefore also have problems due to their high degree of unsaturation which call for treatments to increase stability against oxidation and/or through elimination of important part of the constitution of the oil resulting in loss in its nutritional value.

Added to the above problems of heat stability of poly unsaturated fatty acids and possible deterioration and exposure to air and moisture there is also the additional problems of providing the beneficial actives EPA/DHA in pure form for its possible use and application in environments requiring heat stability. Alpha linolenic acid (ALNA) through bio-synthesis pathway can theoretically produce EPA/DHA but their conversion is insignificant because of deficiency in respective enzymes. Clinical trial with soyabean oil (8% ALNA) or canola (12% ALNA) has reported that ALNA is not effective to reduce triglyceride levels possibly due to insignificant availability of the beneficial actives EPA/DHA from such source.

At present there are two major sources of EPA/DHA, namely fish oil and algae Enrichment of EPA/DHA in fish oil is generally done by fractional distillation and related procedures but during this process it is likely to produce unidentified side products.

For such problems of pure source of EPA/DHA in desired concentration the effective valuable therapeutic use of EPA/DHA ion a form suitable for regular consumption/application/administration has not been possible over the years. It is found that maximum purity of about 70% of EPA/DHA is at most made available to the art as of now and thus the impurity content in sources of EPA/DHA in turn has continued to affect its possible valuable wide scale therapeutic use/application.

The problem of purity of EPA/DHA from its available sources and in particular the impurity content in such presently available sources of EPA/DHA make it extremely difficult to favour its possible applications for its therapeutic benefits especially in controlling triglyceride and cholesterol levels in the body by its regular intake/consumption. It would be clearly evident from the above state of art that the impurity levels in the available sources of EPA/DHA not only make its use/application limited but also has been found to be not acceptable in the art in as far as its possible uses in environments/mediums involving high temperatures such as dietary edible oils.

Thus, the above reveal that while on one hand it is desired to make advantageous use of the therapeutic values of EPA and DHA in controlling triglycerides/cholesterol levels in the body by way of its provision in a medium/formulation suitable for regular consumption the same has been difficult to achieve due to the inherent unsaturated form and consequently, therefore, possible unstable characteristics and also the limitations in providing the same in pure form suitable for such regular and wide scale applications and uses especially for maintenance of health and safe living.

OBJECTS OF THE INVENTIONS

It is thus the basic object of the invention to provide for the availability of EPA/DHA in heat and storage stable formulation free of any encapsulated/protected form which would enable its direct and possible regular administration/delivery in humans for effective and advantageous use of its therapeutic values.

Another object of the present invention is directed to avoid the limitation of the presently available (not 100% pure) form of EPA/DHA in its effective use in wide variety of therapeutically valuable formulations including heat stable formulations such as dietary cooking oil and thereby provide for the much desired wide scale use and application of the therapeutic values of EPA/DHA.

Yet another object of the present invention is directed to identify selective stable dietary edible oil formulation having selective amounts of EPA/DHA which would maintain the later synergistically stable and maintain its therapeutic values in such stable form.

Yet another object of the present invention is directed to identify selective heat stable dietary edible oil formulation having selective amounts of EPA/DHA which would maintain the later synergistically stable and maintaining its therapeutic values in the heat stable form.

Yet another object of the present invention is directed to therapeutically valuable heat stable cooking media incorporating EPA/DHA in a form % which would be stable including heat and storage stability and be consumer friendly for large scale use and application in maintenance of health and well-being of individuals.

Yet further object of the present invention is directed to a surprising and synergistically heat stable dietary edible oil including triglyceride/cholesterol controlling highly unsaturated EPA/DHA which would serve as an edible cooking media and which upon regular consumption would favour at least one of 1) reducing the low density lipo-protein (LDL) to control cholesterol levels,
2) elevate high density lipo-protein (HDL) or lower the ratio of cholesterol to direct HDL to favour effective disposal of accumulated cholesterol,
3) reduces the triglycerides level in the body and
4) reduce tendency of platelets to clump and adhere to the blood vessel walls and related contraction of the blood vessels themselves because of lower concentration of cholesterol in the blood stream.

Yet another object of the present invention is directed to the development of a selective dietary edible cooking oil and in particular to a heat stable dietary edible oil incorporating EPA/DHA from available sources and maintaining the fatty acid distribution in the oil to desired levels to maintain health and well-being of humans consuming such edible oil on regular basis.

Yet another object of the present invention is directed to the study of the characteristic of EPA/DHA and its highly unsaturated constitution and confirm possible end use/application of the same in environment/media in which EPA/DHA could not be provided due to its available knowledge on highly unsaturated characteristics and possible unstable form.

SUMMARY OF THE INVENTION

Thus according to the basic aspect of the present invention, there is provided a synergistically heat stable therapeutically active triglyceride and cholesterol controlling cooking oil composition comprising atleast one source of atleast one of Eicosa Penataenoic Acid (EPA) and Docosa Hexaenoic Acid (DHA), said Eicosa Pentaenoic Acid and Docosa Hexaenoic Acid being of atleast 50% to less than 100% purity in a free of any encapsulated form in combination with synergistically stability contributing edible cooking oil constituents/ingredients.

It has surprisingly been found by way of the present invention that the limitations in use/application of the presently available sources of Eicosa Pentaenoic Acid and Docosa Hexaenoic Acid (not 100% pure) which includes impurities contributing towards the instability of the therapeutically beneficial activity of EPA/DHA in formulations can be avoided and a stable more importantly heat stable dietary edible oil can be obtained from such presently available sources of EPA/DHA maintaining desired heat stability.

The dietary edible cooking oil blend is thus found to synergistically facilitate the presently available forms of EPA and DHA in the oil media thereby avoiding its limitations and providing for a suitable form of such therapeutically active health benefiting agents to serve the purpose of controlling triglyceride/cholesterol on regular consumption.

In accordance with a preferred aspect of the present invention there is provided a synergistically heat stable therapeutically active triglyceride and cholesterol controlling cooking oil composition comprising atleast one source of atleast one of Eicosa Penataenoic Acid (EPA) and Docosa Hexaenoic Acid (DHA) in amounts of up to 7%, said Eicosa Pentaenoic Acid and Docosa Hexaenoic Acid being of atleast 50% to less than 100% purity in a free of any encapsulated form in combination with synergistically stability contributing edible cooking oil constituents/ingredients.

Importantly it is thus the finding of the present invention that by way of the above selective incorporation of the therapeutically active EPA/DHA from the available sources (not 100% pure) it is possible to synergistically reduce the unwanted unstable constituents of the formulation within safe limits to thereby make it suitable for human consumption. Importantly, further such possible reduction in the unwanted unstable constituents in the formulation involving the therapeutically active EPA and DHA is found to be also heat stable, apart from being within safe limits for human consumption, beyond the ambient temperature to the usual cooking temperature.

According to a preferred aspect of the present invention, there is provided a synergistically heat stable therapeutically active health benefiting dietary edible cooking oil composition comprising atleast one source of atleast one of Eicosa Pentaenoic Acid and Docosa Hexaenoic Acid, atleast 50% to less than 100% purity in amounts of up to 7%, free of any encapsulated form in combination with synergistically heat stability contributing edible cooking oil constituents 1 ingredients.

In accordance with yet another aspect of the present invention the same is directed to provide heat stable dietary edible cooking oil composition comprising one source of atleast one of Eicosa Penataenoic Acid (EPA) and Docosa Hexaenoic Acid (DHA), said Eicosa Pentaenoic Acid and Docosa Hexaenoic Acid being atleast 50% to less than 100% purity in a free of any encapsulated form in combination with synergistically heat stability contributing edible cooking oil constituents/ingredients comprising a fatty acid distribution of saturated fatty acids (SFA) 15-20%,
mono unsaturated fatty acids (MUFA) 40-65%, and
Polyunsaturated fatty acids (PUFA) 20-35% including said EPA/DHA.

In accordance with further preferred aspect of the present invention the same is directed to provide heat stable dietary edible cooking oil composition comprising one source of atleast one of Eicosa Penataenoic Acid (EPA) and Docosa Hexaenoic Acid (DHA) in amount of up to 7%, said Eicosa Pentaenoic Acid and Docosa Hexaenoic Acid being atleast 50% to less than 100% purity in a free of any encapsulated form in combination with synergistically heat stability contributing edible cooking oil constituents/ingredients comprising a fatty acid distribution of:

a) saturated fatty acids (SFA) 15-20%,
b) mono unsaturated fatty acids (MUFA) 40-65%, and
c) Polyunsaturated fatty acids (PUFA) 20-35% including said EPA/DHA.

It is thus surprisingly found by way of the present invention that the said highly unsaturated and presumably unstable Eicosa Pentaenoic Acid and/or Docosa Hexaenoic Acid in an oil media can synergistically take care of the highly unsaturated and consequentially easily oxidisable and unstable characteristic of EPA/DHA enabling provision of the said benefit actives free of its usual encapsulated form. Importantly, the above findings of the invention further lead to the provision of dietary edible cooking oil involving the EPA/DHA in a heat stable and therapeutically active form.

The invention is therefore directed to provide the much desired alternative and more convenient root for consumption of the required EPA/DHA on a regular basis to make beneficial use of the known health benefits of such EPA/DHA as a triglyceride/cholesterol controlling agent. Thus the dietary blend containing EPA/DHA of the invention on one hand maintains the desired constitution of edible oil as well as the highly unsaturated EPA/DHA which can be used for cooking purposes and on the other hand impart the desired health and safety benefits to the basic dietary edible cooking oil through incorporation of the therapeutically valuable EPA/DHA from its usual sources and without the need for any protective encapsulation and thereby favour:

a) reducing the low density lipo-protein (LDL) to control cholesterol levels
b) elevate high density lipo-protein another fat derivative (HDL) or lowering the ratios of LDL and HDL to favour effective disposal of accumulated cholesterol
c) reduce the triglyceride levels and
d) reduce tendency of platelets to clump and adhere to the blood vessel walls and related contraction of the blood vessel themselves because of lower concentration of cholesterol in blood streams.

According to the invention the synergistically heat stable therapeutically active triglyceride and cholesterol controlling cooking oil composition of the invention can be obtained following simple blending of the selected source of atleast one of Eicosa Pentaenoic Acid and Docosa Hexaenoic Acid (DHA) in synergistically stability contributing edible cooking oil constituents/ingredients.

In accordance with another aspect there is provided a process for manufacture of EPA/DHA fortified synergistically heat stable therapeutically active triglyceride and cholesterol controlling dietary edible cooking oil formulation comprising: incorporating the highly unsaturated EPA/DHA from available sources purity atleast 50% and less than 100% free of any encapsulated form in the heat stability contributing edible oil constituents/ingredients such as to maintain desired stability of the EPA/DHA in usual cooking temperatures.

In accordance with the preferred aspect there is provided a process for manufacture of EPA/DHA fortified synergistically heat stable therapeutically active triglyceride and cholesterol controlling dietary edible cooking oil formulation comprising:

incorporating the highly unsaturated EPA/DHA from available sources purity atleast 50% and less than 100% in amounts of upto 7% free of any encapsulated form in the stability contributing edible oil constituents/ingredients such as to maintain desired stability of the EPA/DHA in usual cooking temperatures.

In accordance with another aspect of the invention there is provided a process for manufacture of EPA/DHA fortified synergistically heat stable therapeutically active triglyceride and cholesterol controlling heat stable dietary edible cooking oil comprising selecting the fatty acid distribution such that Saturated Fatty Acids (SFA) comprise 15-20%;
Mono Unsaturated Fatty Acids (MUFA) comprises 40-65%; and
Polyunsaturated Fatty Acids (PUFA) comprises 20-35% including said EPA/DHA.

The cooking oil source in the blend can include conventional vegetable oils such as groundnut oil, ricebran oil, soyabean oil, corn oil, palm oil and the like or mixtures thereof.

The blend can additionally incorporate other known additives to conventional dietary edible oils permitted anti-oxidants such as "TBHQ, BHA and TOCOPFEROLS, etc.

The sources of Eicosa Pentaenoic Acid (EPA) and Docosa Hexaenoic Acid (DHA) can include conventional sources such as fish oil, algae oil, marine mammals, sea fish, sea birds and the like or derivatives thereof.

It is possible to further refine the above selective blend of the dietary edible oil invention incorporating EPA/DHA followed by deodorisation using standard refining procedures.

In accordance with yet another aspect of present invention, there is provided a synergistically heat stable therapeutically active health benefiting dietary cooking oil composition comprising atleast one source of atleast one of Eicosa Pentaenoic Acid and Docosa Hexaenoic Acid, in amounts of upto 20%, free of any encapsulated from in combination with synergistically heat stability contributing edible cooking oil constituents/ingredients According to this aspect of the invention, it has surprisingly been found that the highly unsaturated and possible easily oxidized form of DHA and EPA contrary to such general belief when incorporated in oil formulations, the same could avoid the problems of its deterioration resulting from the high degree of unsaturation and provide for a synergistically heat stable dietary edible oil incorporating such therapeutically beneficial EPA/DHA. The invention therefore teaches away from the established belief that the highly unsaturated and deteriorating EPA/DHA cannot be used in dietary edible oils especially dietary edible oils for cooking purposes and surprisingly provides for a safe and heat stable dietary edible cooking oil formulation incorporating such unstable therapeutic actives the EPA/DHA.

EXAMPLES

The details of the inventions, its objects and advantages are explained hereunder in greater details in relation to non-limiting exemptory illustrations as per the following examples;

Example I

The heat stability of the highly unsaturated and easily oxidisable EPA/DHA in the oil blend of the invention, EPA/DHA from available sources of enriched fish oil was blended with groundnut oil in various proportions and the stability of the formulations tested is importantly to further confirm the unexpected and synergistic heat stability achieved by the oil formulation of the invention incorporating the EPA/DHA, oil blends with varying amount of active benefit agent EPA/DHA heated from ambient to upto 220 deg.C were tested. To maximize the process of deterioration, apart from heating at 180 deg.C, 200 deg.C and 220 deg. C., air was incorporated during heating by using a magnetic stirrer. The results obtained are reproduced hereunder in Table I.

TABLE I

Fatty Acid Composition of oils before and after heating at 180° C., 200° C. and 220° C. by Gas Liquid Chromatography

| | A | | | | B | | | | C | | | |
|---|---|---|---|---|---|---|---|---|---|---|---|---|
| FA | Amb | 180° C. | 200° C. | 220° C. | Amb | 180° C. | 200° C. | 220° C. | Amb | 180° C. | 200° C. | 220° C. |
| 16:0 | 9.4 | 9.1 | 8.7 | 6.6 | 8.3 | 8.7 | 6.2 | 8.0 | 7.5 | 7.6 | 6.8 | 7.4 |
| 18:0 | 2.8 | 2.8 | 2.8 | 2.8 | 2.7 | 2.7 | 2.6 | 2.6 | 2.5 | 2.5 | 2.5 | 2.5 |
| 18:1 | 54.6 | 55.3 | 55.1 | 55.1 | 50.4 | 51.5 | 50.7 | 50.9 | 45.8 | 46.4 | 45.1 | 45.5 |
| 18:2 | 21.4 | 21.1 | 21.3 | 21.2 | 19.7 | 19.9 | 20.0 | 19.9 | 18.0 | 18.0 | 17.8 | 18.1 |
| 20:0 | 1.4 | 1.5 | 1.5 | 1.5 | 1.5 | 1.5 | 1.5 | 1.5 | 1.6 | 1.6 | 1.8 | 1.6 |
| 20:1 | 1.2 | 1.2 | 1.3 | 1.3 | 1.2 | 1.2 | 1.2 | 1.2 | 1.1 | 1.1 | 1.2 | 1.1 |
| 20:4 | — | — | — | — | — | 0.2 | — | — | 0.4 | 0.4 | 0.2 | 0.2 |
| 20:5 | 3.5 | 3.5 | 3.6 | 3.7 | 3.9 | 4.3 | 4.4 | 4.6 | 5.0 | 5.6 | 6.1 | 5.6 |
| 22:5 | — | — | — | — | 0.4 | 0.4 | 0.4 | 0.4 | 0.6 | 0.6 | 0.6 | 6.6 |
| 24:0 | 1.4 | 1.4 | 1.5 | 1.6 | 1.6 | 1.2 | 1.4 | 1.4 | 1.8 | 1.6 | 1.9 | 16 |
| 22:6 | 3.4 | 3.2 | 3.5 | 3.4 | 7.4 | 6.9 | 7.4 | 7.2 | 11.3 | 11.2 | 12.2 | 11.3 |
| unknown | 0.9 | 0.9 | 0.7 | 0.8 | 2.9 | 1.5 | 2.2 | 2.3 | 4.4 | 3.4 | 3.8 | 4.5 |

| | | D | | | | E | | | |
|---|---|---|---|---|---|---|---|---|---|
| | FA | Amb | 180° C. | 200° C. | 220° C. | Amb | 180° C. | 200° C. | 220° C. |
| | 16:0 | 7.2 | 7.5 | 6.4 | 6.7 | 2.7 | 2.0 | 1.9 | 1.8 |
| | 18:0 | 2.4 | 2.4 | 2.3 | 2.3 | 1.7 | 1.4 | 1.2 | 1.2 |
| | 18:1 | 41.5 | 42.4 | 40.4 | 41.4 | 8.9 | 7.2 | 6.8 | 6.4 |
| | 18:2 | 16.7 | 17.1 | 16.0 | 16.4 | 5.4 | 4.5 | 4.4 | 4.2 |
| | 20:0 | 1.7 | 1.7 | 1.7 | 1.7 | 2.7 | 2.3 | 2.3 | 2.1 |
| | 20:1 | 1.0 | 1.0 | 1.0 | 1.0 | 0.2 | 0.4 | 0.6 | 0.5 |
| | 20:4 | 0.5 | 0.6 | 0.3 | 0.3 | 1.7 | 1.6 | 0.9 | 0.9 |
| | 20:5 | 6.8 | 6.6 | 6.8 | 6.8 | 15.0 | 14.5 | 15.3 | 14.4 |
| | 22:5 | 0.8 | 0.8 | 0.8 | 0.8 | 2.4 | 2.5 | 2.7 | 2.4 |
| | 24:0 | 1.5 | 1.3 | 1.9 | 1.7 | 1.9 | 1.9 | 1.5 | 1.7 |
| | 22:6 | 15.8 | 15.0 | 15.6 | 15.6 | 42.4 | 45.3 | 48.9 | 45.7 |
| | unknown | 4.1 | 3.6 | 6.8 | 5.3 | 15.0 | 16.4 | 13.4 | 18.7 |

A - 10% Fish Oil + 90% Groundnut Oil – EPA/DHA = 6.9% SFA – 15%: MUFA – 55.8%: PUFA – 28.3%
B - 20% Fish Oil + 80% Groundnut Oil – EPA/DHA = 11.3% SFA – 14.1%: MUFA – 51.6%: PUFA – 31.4%
C - 30% Fish Oil + 70% Groundnut Oil – EPA/DHA = 16.3% SFA – 13.4%: MUFA – 46.9%: PUFA – 35.3%
D - 40% Fish Oil + 60% Groundnut Oil – EPA/DHA = 22.6% SFA – 12.8%: MUFA – 42.5%: PUFA – 40.6%
E - Fish Oil 100% – EPA/DHA – 58% SFA – 6.2%: MUFA – 7.6%: PUFA - 64.4%
Amb—Ambient Temperature
EPA—Eicosa Pentaenoic Acid (C20: 5 n – 3)
DHA—Docosa Hexaenoic Acid (C22: 6 n – 3)
SFA—Saturated Fatty Acid
MUFA—Mono-unsaturated Fatty Acid
PUFA—Poly unsaturated Fatty Acid The above results in Table I reveal the synergistic stability contributing effect of the combination of the edible oil with fish oil source of the highly unsaturated and easily oxidisable therapeutically valuable EPA/DHA. In particular as apparent from the results in Table I, in case of 100% fish oil, source of the EPA/DHA even at ambient temperature the deterioration of the product and consequential high levels of unwanted constituents is apparent while advantageously the same fish oil source when selectively blended with the edible oil of the present invention, the same is found to be synergistically stable not only at ambient conditions but even at higher cooking temperatures in the range of 180 deg. C. and above. The notable reduction in the unwanted constituents (unknown) level in the blend of the invention makes it possible for selective and advantageous use of the oil blend incorporating the EPA/DHA of the present invention.

In accordance with the preferred aspect of the invention, not only the unwanted deterioration products (unknown) levels could be synergistically controlled by the oil blend of the invention but importantly also the level of such unwanted deterioration products could be controlled within ver safe and normal levels found in usual edible oils inspite of incorporation of the highly unsaturated EPA/DHA at upto 7%.

The results of Table I, also confirm the unexpected and peculiar findings of the present invention that contrary to the usual belief in the art that due to the high degree of unsaturation the poly unsaturated fatty acids DHA and EPA are easily oxidisable and hence obviously unstable at higher temperatures usual for cooking, such fatty acids DHA and EPA from the fish oil source is found to be surprisingly heat stable even at temperatures of up to 220 deg. C. Such special findings of the invention clearly and sufficiently provide avenues for wide scale use/application of the therapeutically active EPA and DHA even under high temperatures and in medium such as cooking oil requiring stability at such high temperatures.

Example II

To further confirm the constitutional stability of the dietary oil, the blend of the invention, polar material content (indicative of heat damage during heating/cooling) was analysed following American Official Analytical method AOCS-Cd 20-91. Air was incorporated during heating by a magnetic stirrer. The results obtained are reproduced in Tables II and III hereunder.

TABLE II

Percentage Polar Compound of about 11% EPA/DHA from algae source obtained following the above procedure of American Oil Chemists Society (AOCS Cd 20-91) Percentage of Polar Compound identified following the above procedure are:

| Ex. A | Ex. b |
|-------|-------|
| 0.41  | 0.46  |

Ex A: Percentage Polar Compound of about 11% EPA/DHA from algae source
Ex B: Heated for 5 mins. at 180° C.

TABLE III

Percentage Polar Compound of about 13% EPA/DHA from fish oil source obtained following the above procedure of American Oil Chemists Society (AOCS Cd 20-91) Percentage of Polar Compounds identified following the above proceduce are:

| Ex. A | Ex. b |
|-------|-------|
| 9.3   | 10.2  |

Ex A: Percentage Polar Compound of about 13% EPA/DHA from fish oil source
Ex B: Heated for 5 mins. at 180° C.

Importantly, the above results in Table I, II and III therefore clearly and sufficiently confirm the surprising stability including heat stability of the edible oil formulation of the invention including EPA/DHA from available fish oil algae-sources at various temperatures. Thus surprisingly and unexpectedly and importantly contrary to the general belief that the highly unsaturated EPA/DHA would be heat unstable at usual, cooking temperatures, the present invention clearly demonstrates the synergistic beat stability of EPA/DHA in oil media. The invention therefore clearly and sufficiently teaches for the first time the possibility of providing highly unsaturated EPA/DHA in cooking oil formulations as a ready and regular source of intake of the therapeutically active beneficial agents EPA/DHA without the need for an), protective/encapsulated form for safe and healthy use even at higher temperatures such as the ususal cooking temperatures as an effective triglyceride/cholesterol controlling agent.

Example III

To further ascertain the problem of the presently available sources of EPA/DHA such as the fish oil source resulting in unwanted constituents therein leading to problems in its use/application for its effective therapeutic values, the oil blends (A) to (D) of Table I and also the 100% fish oil (E) of Table I were subjected to heating and evaluation of its polar and non-polar constituents. The results are reproduced hereunder in Table IV.

TABLE IV

|           | A (10-40/10) | | B (10-40/20) | | C (10-40/30) | | D (10-40/40) | | E (10-40/100) | |
|-----------|-------|-------|-------|-------|-------|-------|-------|-------|-------|-------|
|           | Polar | Non-Polar | Polar | Non-Polar | Polar | Non-Polar | Polar | Non-Polar | Polar | Non-Polar |
| Amb       | 2.8   | 97.3  | 5.5   | 94.5  | 8.5   | 91.5  | 18.7  | 81.7  | 33.0  | 67.0  |
| 180 deg. C. | 6.5 | 93.5  | 15.2  | 84.8  | 15.4  | 84.6  | 22.0  | 78.0  | 35.0  | 65.0  |
| 200 deg. C. | 10.2 | 89.8 | 15.0  | 85    | 16.8  | 83.2  | 24.0  | 75.6  | 40.7  | 59.3  |
| 220 deg. C. | 11.3 | 88.6 | 15.2  | 84.7  | 17.6  | 82.3  | 24.4  | 75.9  | 41.3  | 58.6  |

The above results in Table IV go to confirm that the fish oil source of EPA/DHA as such is constitutionally not suitable for ready use/application due to its high levels of unwanted constituents (unwanted polar constituents).

The invention and in particular the oil blend tares care of such limitations of presently available fish oil sources of EPA/DHA for imparting therapeutic benefit activity by way of a stability imparting combination with the edible oil source of the present invention. As clearly apparent from the polar/non-polar constituent of the various blends of the invention the same clearly and sufficiently takes care of the desired lowering of the unwanted polar constituents from the fish oil source of EPA/DHA use in the formulations.

The oil blend of the invention in Table IV further demonstrates the unexpected synergistic control over the unwanted polar constituents even at higher temperatures of 180 deg.C+ which is the usual cooking temperature and confirm the workability of the formulation of the inventions for cooling purpose without any deterioration in its constituents.

Example IV

The therapeutic beneficial activity of the oil formulation of the invention incorporating EPA/DHA free of any encapsulated form was further tested by actual clinical (feeding trials) with 3 Nos. of Guinea pigs. The protocol followed for the said tests was as discussed hereunder:

The animals were maintained in animal house receiving standard diet. The experimental oil was heated and added to the mother feed which vas subsequently palletized for feeding of guinea pigs. Initial lipid profile (day 0) were measured for comparison. After four weeks of receiving EPA/DHA, lipid profile was measured again Total amount of EPA/DHA consumed per day per animal in each group were calculated from feed intake and EPA/DHA content in feed.

The results obtained are represented hereunder in Table V and VI.

TABLE V

Day 0 Lipid Profile

UNITS: MG/DL (milligram/deciliter)

| Method | A1 | A2 | A3 | B1 | B2 | B3 | C1 | C2 | C3 |
|---|---|---|---|---|---|---|---|---|---|
| Cholesterol | 46 | 36 | 41 | 44 | 41 | 43 | 39 | 40 | 41 |
| Direct HDL | 4 | 5 | 5 | 5 | 4 | 5 | 4 | 4 | 3 |
| Triglycerides | 51 | 63 | 72 | 81 | 74 | 92 | 44 | 114 | 106 |
| VLDL | 10 | 13 | 14 | 16 | 15 | 18 | 9 | 23 | 21 |
| LDL | 32 | 18 | 22 | 23 | 22 | 20 | 26 | 13 | 17 |
| Ratio | 11.5 | 7.2 | 8.2 | 8.8 | 10.3 | 8.6 | 9.8 | 10.0 | 13.7 |

TABLE VI

Lipid Profile after 4 weeks

UNITS: MG/DL (milligram/deciliter)

| Method | A1 | A2 | A3 | B1 | B2 | B3 | C1 | C2 | C3 |
|---|---|---|---|---|---|---|---|---|---|
| Cholesterol | 43 | 34 | 32 | 43 | 28 | 35 | 26 | 27 | 34 |
| Direct HDL | 4 | 4 | 4 | 5 | 3 | 5 | 3 | 3 | 3 |
| Triglycerides | 55 | 61 | 42 | 47 | 69 | 36 | 53 | 48 | 49 |
| VLDL | 11 | 12 | 8 | 9 | 14 | 7 | 11 | 10 | 10 |
| LDL | 28 | 18 | 20 | 29 | 11 | 23 | 12 | 14 | 21 |
| Ratio | 10.8 | 8.5 | 8.0 | 8.6 | 9.3 | 7 | 8.7 | 9 | 11.3 |

A1, A2, A3 - Animals fed with 0.076 gm of EPA/DHA per day.
B1, B2, B3 - Animals fed with 0.286 gm of EPA/DHA per day.
C1, C2, C3 - Animals fed with 0.46 gm of EPA/DHA per day.
Ratio - Cholesterol divide by Direct HDL The above results under Tables V and VI clearly show not only the surprising stability of the EPA/DHA in the oil formulation of the invention but also confirms the retention of its benefit action upon consumption/administration in reducing cholesterol, triglyceride, LDL etc. after feeding of the oil preparation of the invention incorporating the EPA/DHA on the daily basis.

It is thus possible by way of the invention to provide for alternative media for the availability of EPA/DHA in heat and storage stable form free of its encapsulated form or possible regular consumption/application/administration by human for therapeutic benefits. The invention is further directed to favour beneficial and consumer friendly large scale regular intake/application of benefit actives of EPA/DHA in maintenance of human health and well being especially in controlling triglyceride and cholesterol in the human body for a safe and healthy living.

I claim:

1. A synergistically heat stable therapeutically active triglyceride and cholesterol controlling dietary edible cooking oil composition comprising at least one oil source having at least one of Eicosa Pentaenoic Acid (EPA) and Docosa Hexaenoic Acid (DHA), said Eicosa Pentaenoic Acid (EPA) and Docosa Hexaenoic Acid (DHA) being of at least 50% to less than 100% purity and free of any encapsulated or protected form, in combination with a synergistically stability contributing edible cooking oil having constituents/ingredients comprising Saturated fatty acids (SPA), Mono unsaturated fatty acids (MUFA) and Polyunsaturated fatty acids (PUFA), said dietary edible cooking oil composition is stable at temperatures of 180° C. and above, the composition comprising up to 7% by wt. of the Eicosa Pentaenoic Acid (EPA) and Docosa Hexaenoic Acid (DHA), and having a fatty acid distribution of Saturated fatty acids (SFA) 15-20%, Mono unsaturated fatty acids (MUFA) 40-65%, and Polyunsaturated fatty acids (PUFA) including said EPA/DHA, 20-35%.

2. A synergistically heat stable triglyceride and cholesterol controlling dietary edible cooking oil composition according to claim 1 comprising of Eicosa Pentaenoic Acid (EPA) and Docosa Hexaenoic Acid (DHA) in combined amount of up to 7% by weight of the composition.

3. A synergistically heat stable therapeutically active triglyceride and cholesterol controlling dietary edible cooking oil according to claim 1 wherein said edible cooking oil is selected from any vegetable oil including conventional groundnut oil, rice-bran oil, soybean oil, corn oil, palm oil, or mixtures thereof.

4. A synergistically heat stable therapeutically active triglyceride and cholesterol controlling dietary edible cooking oil as according to claim 1 comprising additionally other known additives to conventional dietary edible oils including permitted anti-oxidants TBHQ. BHA and Tocopherol.

5. A synergistically heat stable therapeutically active triglyceride and cholesterol controling, dietary edible cooking oil composition according to claim 1 wherein the sources of Eicosa Pentaenoic Acid (EPA) and Docosa Hexaenoic Acid (DHA) include conventional sources of fish oil, algae oil, marine mammals, sea fish, sea birds.

6. A process for the manufacture of a synergistically heat stable therapeutically active triglyceride and cholesterol controlling, dietary edible cooking oil composition as claimed in claim 1, comprising:

blending at least one oil source having at least one of Eicosa Pentaenoic Acid (EPA) and Docosa Hexaenoic Acid (DHA) having at least 50% to less than 100% purity in said synergistically stability contributing edible cooking oil, so that the composition is stable at temperatures of 180° C. and above, the composition comprising up to 7% by wt. of the Eicosa Pentaenoic Acid (EPA) and Docosa Hexaenoic Acid (DHA), and having a fatty acid distribution of Saturated fatty acids (SFA) 15-20%, Mono unsaturated fatty acids (MUFA) 40-65%, and Polyunsaturated fatty acids (PUFA), including said EPA/DHA, 20-35%.

* * * * *

UNITED STATES PATENT AND TRADEMARK OFFICE
CERTIFICATE OF CORRECTION

PATENT NO. : 8,114,453 B2
APPLICATION NO. : 11/817973
DATED : February 14, 2012
INVENTOR(S) : Sen Page 1 of 1

It is certified that error appears in the above-identified patent and that said Letters Patent is hereby corrected as shown below:

Column 12 line 41 change: "ing Saturated fatty acids (SPA), Mono unsaturated fatty acids" to:

-- ing Saturated fatty acids (SFA), Mono unsaturated fatty acids --

Column 12 line 44 change: "tures of 180° C. and above, the composition comprising up to" to:

-- tures of 180° C and above, the composition comprising up to --

Column 12 line 65 change: "ted anti-oxidants TBHQ. BHA and Tocopherol." to:

-- ted anti-oxidants TBHQ, BHA and Tocopherol. --

Column 14 line 3 change: "temperatures of 180° C. and above, the composition" to:

-- temperatures of 180° C and above, the composition --

Signed and Sealed this
Twenty-eighth Day of May, 2013

Teresa Stanek Rea
*Acting Director of the United States Patent and Trademark Office*